US011732004B2

(12) United States Patent
Zurlo et al.

(10) Patent No.: US 11,732,004 B2
(45) Date of Patent: Aug. 22, 2023

(54) COMPOSITIONS AND METHODS FOR SIMPLIFIED HIGH EFFICIENCY ISOLATION OF PROTEINS

(71) Applicant: PLASMA TECHNOLOGIES, LLC, Charleston, SC (US)

(72) Inventors: Eugene Zurlo, Charleston, SC (US); Dennis Curtin, Plattsburgh, NY (US); Klaus Peter Radtke, Charleston, SC (US); Kurt L. Brillhart, Mission Viejo, CA (US)

(73) Assignee: Plasma Technologies, LLC, Charleston, SC (US)

( * ) Notice: Subject to any disclaimer, the term of this patent is extended or adjusted under 35 U.S.C. 154(b) by 191 days.

(21) Appl. No.: 17/225,934

(22) Filed: Apr. 8, 2021

(65) Prior Publication Data
US 2021/0317163 A1    Oct. 14, 2021

Related U.S. Application Data

(60) Provisional application No. 63/008,365, filed on Apr. 10, 2020.

(51) Int. Cl.
| | |
|---|---|
| *C07K 1/22* | (2006.01) |
| *C07K 16/00* | (2006.01) |
| *C07K 1/16* | (2006.01) |
| *C07K 16/06* | (2006.01) |
| *C07K 1/30* | (2006.01) |

(52) U.S. Cl.
CPC ............. *C07K 1/22* (2013.01); *C07K 16/00* (2013.01)

(58) Field of Classification Search
None
See application file for complete search history.

(56) References Cited

U.S. PATENT DOCUMENTS

| | | | | |
|---|---|---|---|---|
| 4,256,631 A | * | 3/1981 | Yokoo ................. | C07K 16/065 530/390.5 |
| 4,639,513 A | | 1/1987 | Hou et al. | |
| 6,093,324 A | * | 7/2000 | Bertolini ............. | C07K 16/065 530/416 |
| 10,640,548 B2 | | 5/2020 | Kaar et al. | |
| 2019/0055282 A1 | * | 2/2019 | Zurlo ................... | A61K 35/14 |

FOREIGN PATENT DOCUMENTS

| | | | | |
|---|---|---|---|---|
| CN | 110872345 | | 3/2020 | |
| EP | 2554160 | | 2/2013 | |
| KR | 100924523 | | 11/2009 | |
| WO | WO-2013126904 A1 | * | 8/2013 | ............ A61K 35/16 |
| WO | 201500135884 | | 9/2015 | |

OTHER PUBLICATIONS

Dong, Y. et al., Extraction and purification of IgG by hydrophilic organic solvent salting-out extraction, Journal of Chromatography B, 2016, vol. 1012-1013, pp. 137-143.
International Search Report for PCT Application No. PCT/US2021/026462 dated Jul. 28, 2021, 15 pages.

* cited by examiner

*Primary Examiner* — Daniel E Kolker
*Assistant Examiner* — James L Rogers
(74) *Attorney, Agent, or Firm* — Fish IP Law, LLP (57) ABSTRACT

Compositions and methods are provided that simplify isolation of proteins of interest from serum or plasma. Finely divided silica or a similar lipid/lipoprotein binding solid is used in combination with a protein precipitating agent to generate a solution that includes the protein of interest and that can be applied to chromatography media without resulting in significant fouling of the media. The method is particularly suitable for isolation of immunoglobulin G.

20 Claims, 8 Drawing Sheets

COMPOSITIONS AND METHODS FOR SIMPLIFIED HIGH EFFICIENCY ISOLATION OF PROTEINS

This application claims the benefit of U.S. Provisional Patent Application No. 63/008,365 filed on Apr. 10, 2020. This and all other referenced extrinsic materials are incorporated herein by reference in their entirety. Where a definition or use of a term in a reference that is incorporated by reference is inconsistent or contrary to the definition of that term provided herein, the definition of that term provided herein is deemed to be controlling.

FIELD OF THE INVENTION

The field of the invention is preparation of immunoglobulin G from blood products, in particular utilizing affinity chromatography.

BACKGROUND

The background description includes information that may be useful in understanding the present invention. It is not an admission that any of the information provided herein is prior art or relevant to the presently claimed invention, or that any publication specifically or implicitly referenced is prior art.

Administration of plasma or serum from individuals that have recovered or are convalescing from infection have been used to provide transient passive immunization for infected individuals. Such passive immunization can be traced back to the early 20th century, when specific antibodies were derived from serum obtained from vaccinated animals. Human blood was also identified as a source of antibodies. Such passive immunization provides immediate and short-term immunization against pathogens by providing pathogen-specific antibodies. Since its introduction such passive immunization has proven to be lifesaving for many acute infections. Although antibiotics have largely replaced passive immunization in the treatment of bacterial infections it remains an important tool in the treatment of many viral pathogens, when vaccines or other specific treatments are not available. Notably, such passive immunization has been explored as a treatment for Ebola and Coronavirus infections.

Convalescent blood products are typically obtained through the collection of whole blood or plasma from a previously infected individuals who has developed an effective humoral immunity against the pathogen responsible for the disease in question, and can provide a source of specific human antibodies. Infusion of such convalescent blood products can effectively neutralize a pathogen and assist in removing it from circulation. Different convalescent or hyperimmune blood products have been used to provide such passive immunity, including convalescent whole blood, convalescent plasma, and convalescent serum.

Convalescent plasma has been the subject of increasing attention, for example in the treatment of SARS and related coronaviruses. Plasma obtained by apheresis is currently preferred, as larger volumes can be collected per session, more frequent donations are possible, and the fact there is little to no impact on the donor's hemoglobin levels (due to reinfusion of the red blood cells). Passive immunization with such blood products, however, is not without risk to the recipient. These risks are associated with transfer of blood substances, and include inadvertent infection with other infectious disease agents and reactions to serum constituents, including immunological reactions such as serum sickness. With modern blood banking practices and blood typing the risks of inadvertently transferring known infectious agents or triggering transfusion reactions are low, however in instances where the number of convalescent or recovered individuals is limited such practices may be relaxed. In addition, convalescent sera or plasma used to provide passive immunity is likely be administered to individuals suffering from pulmonary disease, in whom plasma infusion carries a risk for transfusion-related acute lung injury.

Accordingly, there is increasing interest in isolating immunoglobulins (typically IgG) from blood products obtained from convalescing or hyperimmune sources, followed by administration of relatively pure (e.g., greater than 95%) immunoglobulin to sick individuals. This approach can provide the desired passive immunity while avoiding complications caused by the introduction of other blood product components. In addition, IgG so isolated can be lyophilized and reconstituted prior to use, which simplifies both storage and distribution.

An additional benefit of use of isolated hyperimmune immunoglobulins is ability to use smaller volumes relative to hyperimmune plasma infusions. Administration of therapeutic plasma is necessarily limited by the volume of the plasma (unless patient plasma is removed, i.e., plasma replacement). Administration of plasma is a medically involved procedure, particularly where plasma replacement is used, which effectively limits the dose of IgG that can be administered. In contrast, administration of isolated hyperimmune antibodies is not limited in this fashion due to their concentration. The resulting small volume allow safe and convenient administration of higher doses of therapeutic IgG than can be achieved by infusion of hyperimmune serum.

Unfortunately, isolation of IgG from blood products at the requisite purity is a complex process. Typical methods include several precipitation steps, during which IgG can be lost, and can include steps that are not amenable to large scale production. For example, affinity chromatography (e.g., using a protein A or protein G affinity media) is an attractive approach for providing high purity IgG in a limited number of steps. Unfortunately, chromatography columns of such affinity media are prone to fouling with lipids, non-IgG blood proteins, etc. This fouling greatly reduces the capacity of expensive affinity media, and can require lengthy column cleaning steps that can degrade performance over time and reduce the number of cycles for which this costly media is useful. Accordingly, current methods utilizing such IgG-specific affinity chromatography typically incorporate lengthy and complex processing of blood products prior to introduction to the affinity media, which limits its utility.

Thus, there is still a need for compositions and methods that simplify and streamline upstream processing steps when affinity chromatography is utilized for isolating blood proteins.

SUMMARY OF THE INVENTION

The inventive subject matter provides apparatus, systems and methods that simplify preparation of a blood product for application to a chromatography media. Silica granules or powder is added to the blood product along with an organic salt (e.g., a citrate or acetate salt), resulting in precipitate and supernatant fractions. The supernatant fraction can be applied directly to a chromatographic separation step with either no additional processing or minor processing.

One embodiment of the inventive concept is a method of isolating a protein (e.g., immunoglobulin G/IgG) from a blood product by contacting the blood product with a lipid/lipoprotein adsorbent material such as finely divided silica (e.g., fumed silica) and/or other lipophilic and/or inert protein adsorbing materials (e.g., a charged silica, charcoal, activated carbon, $Al(OH)_3$, bentonite, calcium phosphate/hydroxyapatite), while the blood product is mixed with an organic salt, at a concentration that produces a first precipitate and a first supernatant. The finely divided silica and the organic salt can be added in any order, or simultaneously. The first supernatant is applied to a separation column, and a fraction containing the protein of interest (e.g., IgG) is collected from the separation column. In some embodiments an additional protein (such as non-IgG protein) can be recovered from the flowthrough fraction from the separation column. Suitable separation columns can include an affinity media, an anion exchange media, a cation exchange media, a hydrophobic interaction media, a dye affinity media, a mixed mode media, and/or a size exclusion media.

The concentration of the organic salt used is sufficient to precipitate a first non-protein of interest protein (e.g., a non-IgG protein) from the blood product, for example from about 5% to about 20% by weight. The first precipitate includes the finely divided silica and non-protein of interest protein. In some embodiments the first precipitate is resuspended or redissolved to generate a secondary solution that includes first non-IgG protein(s). This secondary solution can be separated from the finely divided silica and further processed to recover a non-protein of interest protein from the secondary solution.

Another embodiment is a method of isolating a protein of interest (e.g., IgG) from a blood product by contacting the blood product with a finely divided silica (e.g., fumed silica) while the blood product is combined with an organic salt (e.g., a citrate or acetate salt), at a concentration that produces a first precipitate (which can include finely divided silica and non-protein of interest protein and a first supernatant. In some embodiments the organic salt is added to the blood product prior to adding the finely divided silica. This first concentration of the organic salt is sufficient to precipitate non-protein of interest protein from the blood product (e.g., from about 5% to about 15% by weight). An additional amount of the organic salt is added to the first supernatant to provide a second concentration of the organic salt, which generates a second precipitate and a second supernatant. In some embodiments non-protein of interest protein is isolated from this second supernatant. The second precipitate is resuspended or redissolved to generate a redissolved second precipitate, which is in turn applied to a separation column. Such a separation column can include affinity media, an anion exchange media, a cation exchange media, a hydrophobic interaction media, a dye affinity media, a mixed mode media, and/or a size exclusion media. A protein of interest (e.g., IgG) containing fraction is then collected from the separation column. In some embodiments a flowthrough fraction is collected from the separation column and is further processed to isolate a non-protein of interest protein.

Some of such embodiments include resuspending the first precipitate to generate a secondary solution that includes non-protein of interest protein, and separating the secondary solution from the finely divided silica. Non-protein of interest protein can subsequently be recovered from the secondary solution.

Another embodiments of the inventive concept is a method of isolating a protein of interest (e.g., IgG) from a blood product by contacting the blood product with an organic salt (e.g., a citrate or acetate salt) at a first concentration (which is sufficient to precipitate non-protein of interest protein from the blood product, for example from about 5% to about 15% by weight) to produce a first precipitate (which can include non-protein of interest protein) and a first supernatant, followed by adding a finely divided silica (e.g., fumed silica) and an additional amount of the organic salt to the first supernatant to provide a second concentration of the organic salt. The finely divided silica can be added after or essentially contemporaneously with addition of the organic salt to the blood product. This generates a second precipitate (which includes protein of interest (e.g., IgG) and the finely divided silica) and a second supernatant (which can include non-protein of interest protein). In some embodiments, non-IgG protein is recovered from this second supernatant. The second precipitate is resuspending and dissolved to generate a redissolved second precipitate and a residual precipitate (which includes the finely divided silica). The redissolved second precipitate is applied to a separation column and an IgG containing fraction is collected from the separation column. In some embodiments a flowthrough fraction is collected that includes non-protein of interest protein is collected from the separation column; such non-protein of interest protein can subsequently be isolated from the flowthrough fraction. Suitable separation columns can include an affinity media, an anion exchange media, a cation exchange media, a hydrophobic interaction media, a dye affinity media, a mixed mode media, and/or a size exclusion media.

In some of such embodiments the first precipitate is resuspended and redissolved to generate a secondary solution containing non-IgG protein. The non-IgG protein is subsequently recovered from the secondary solution.

Various objects, features, aspects and advantages of the inventive subject matter will become more apparent from the following detailed description of preferred embodiments, along with the accompanying drawing figures.

BRIEF DESCRIPTION OF THE DRAWINGS

FIGS. 1A and 1B schematically depict an exemplary methods of the inventive concept.

FIGS. 2A and 2B schematically depict alternative embodiments of a method of the inventive concept.

FIGS. 3A, 3B, and 3C schematically depict an alternative embodiment of a method of the inventive concept, with FIG. 3B continuing from FIG. 3A and FIG. 3C depicting an alternative continuation of FIG. 3A.

DETAILED DESCRIPTION

The inventive subject matter provides apparatus, systems and methods in which a lipid and/or lipoprotein removal and protein precipitation steps are applied in combination to a blood product, for example as a processing step that is upstream from a chromatography separation step (e.g., an affinity chromatography step), from which a protein of interest is obtained in either an eluted fraction or a flow-through fraction. This simplifies upstream processing of blood products while reducing and/or eliminating fouling of chromatography media (such as IgG-specific affinity media). Reduced fouling of the chromatography media preserves the capacity of the media (allowing for the use of less media than would otherwise be possible with reduced processing steps) and/or a reduced need for cleaning of the chromatography media.

Various objects, features, aspects and advantages of the inventive subject matter will become more apparent from the following detailed description of preferred embodiments, along with the accompanying drawing figures in which like numerals represent like components.

In some embodiments, the numbers expressing quantities of ingredients, properties such as concentration, reaction conditions, and so forth, used to describe and claim certain embodiments of the invention are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the invention are approximations, the numerical values set forth in the specific examples are reported as precisely as practicable. The numerical values presented in some embodiments of the invention may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise.

The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided with respect to certain embodiments herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. One or more members of a group can be included in, or deleted from, a group for reasons of convenience and/or patentability. When any such inclusion or deletion occurs, the specification is herein deemed to contain the group as modified thus fulfilling the written description of all Markush groups used in the appended claims.

One should appreciate that the disclosed compositions and methods provide many advantageous technical effects including reducing the economic impact of utilizing chromatography separation steps, in particular the use of IgG-specific affinity chromatography media in the large scale production of specific immune IgG for therapeutic purposes. This has the benefit of making such material more generally available.

The following discussion provides many example embodiments of the inventive subject matter. Although each embodiment represents a single combination of inventive elements, the inventive subject matter is considered to include all possible combinations of the disclosed elements. Thus, if one embodiment comprises elements A, B, and C, and a second embodiment comprises elements B and D, then the inventive subject matter is also considered to include other remaining combinations of A, B, C, or D, even if not explicitly disclosed.

In methods of the inventive concept a blood product is contacted or is in contact with a protein precipitating agent at the same time that the blood product is in contact with a lipid/lipoprotein adsorbing solid. Suitable blood products include serum, plasma (e.g., fresh or non-frozen plasma, cryo-poor plasma from which cryoprecipitate is removed, and previously frozen plasma in which cryoprecipitate has been redissolved, etc.), and intermediate products from blood protein fractionation methods (e.g., Cohn precipitation, ammonium sulfate precipitation, organic salt precipitation, etc.). Such intermediate products can be a supernatant from a precipitation step or, alternatively, a resuspended and redissolved precipitate from a precipitation step.

Suitable precipitating agents include, but are not limited to, organic solvents (e.g., alcohol, acetone, etc.), hydrophilic polymers (e.g., polyethylene glycol, polyvinylpyrrolidone, dextran, etc.), inorganic salts (sodium chloride, sodium sulfate, ammonium sulfate, sodium phosphate, ammonium phosphate, etc.), and/or salts of organic acids (citrate salts, acetate salts, etc.).

Suitable lipid/lipoprotein adsorbing solids can have an ability adsorb lipids, lipoproteins, and/or other contaminants and be available in a finely divided form (e.g., having a mean diameter of less than 5 mm, 4 mm, 3 mm, 2 mm 1 mm, 800 µm, 500 µm, 300 µm, 100 µm, or 50 µm). The density of such solids can be greater than, less than, or substantially similar (i.e., within 10%) to the density of the aqueous solution with which they are used Suitable lipid/lipoprotein adsorbing solids include (but are not limited to) hydrophobic chromatography media, hydrophobic interaction chromatography media, silica (e.g., fumed silica, finely divided silica, charged silica, etc.), charcoal, activated carbon, $Al(OH)_3$, bentonite, and/or calcium phosphate/hydroxyapatite. In a preferred embodiment of the inventive concept the blood product is plasma, the precipitant is a citrate salt, and the lipid/lipoprotein adsorbing solid is fumed silica.

In embodiments of the inventive concept a precipitating agent can be added to a blood product prior to introduction of a lipid/lipoprotein adsorbing solid. For example, in such an embodiment a precipitating agent can be added to a blood product about 5 minutes to about 1 hour prior to addition of a lipid/lipoprotein adsorbing solid (without an intervening separation step). In other embodiments a precipitating agent can be added to a blood product at about the same time as the introduction of a lipid/lipoprotein adsorbing solid. For example, in such an embodiment a precipitating agent can be added within about ±5 minutes of the addition of a lipid/lipoprotein adsorbing solid (without an intervening separation step). In still other embodiments a precipitating agent can be added to a blood product after introduction of a lipid/lipoprotein adsorbing solid. For example, in such an embodiment a precipitating agent can be added to a blood product about 5 minutes to about 1 hour after addition of a lipid/lipoprotein adsorbing solid to the blood product (without an intervening separation step).

Precipitating agents and lipid/lipoprotein adsorbing solids can be provided as separate formulations. These can be applied to the blood product individually or, alternatively, mixed immediately prior to application. One embodiment of the inventive concept is a formulation that combines one or more precipitating agent(s) with one or more lipid/lipoprotein adsorbing solid(s) in a ratio appropriate for a process step to which these materials are to be applied (see below). This further simplifies methods of the inventive concept by providing a single, combined formulation to a step combining protein precipitation and lipid and/or lipoprotein removal.

Precipitating agents can be utilized at any suitable concentration, and the range of concentrations can vary depending upon the nature of the precipitating agent, the blood product used, the lipid/lipoprotein adsorbing solid used, the order and/or timing of precipitating agent and lipid/lipoprotein adsorbing solid addition, and/or the stage of the isolation process at which the precipitating agent is introduced. For example, when applying a citrate salt to plasma in order to precipitate at least a portion of the non-IgG protein content while leaving IgG in solution the citrate salt can be provided at from about 5% to about 15% by weight. Alternatively, when applying a citrate salt to plasma in order to precipitate most or all of the IgG content the citrate salt can be provided at from about 15% to about 50% by weight. The concentration of precipitating agent can be optimized in order to provide maximum retention of IgG in the desired fraction (i.e., either supernatant or precipitate, depending upon the process) while minimizing fouling of a downstream affinity column.

Similarly, lipid and/or lipoprotein adsorbing solids can utilize at any suitable concentration, and the range of concentrations can vary depending upon the nature of the lipid/lipoprotein adsorbing solid, the nature of the precipitating agent, the blood product used, the order and/or timing of precipitating agent and lipid/lipoprotein adsorbing solid addition, and/or the stage of the isolation process at which the lipid/lipoprotein adsorbing solid is introduced. In some embodiments lipid and/or lipoprotein content of the blood product can be characterized prior to processing and the amount of lipid and/or lipoprotein adsorbing solid adjusted accordingly. For example, when applying fumed silica to plasma having typical lipid and/or lipoprotein content the amount can range from about 10 mg per mL plasma to about 500 mg per mL plasma. This amount can be adjusted up to 750 mg per mL plasma or more when the plasma has a high lipid and/or lipoprotein content.

Chromatographic separation steps performed after such treatment can serve to isolate or further purify IgG or other proteins of interest can be utilize positive selection or negative selection of the desired protein species.

In positive selection the IgG or other protein of interest binds to the chromatography media, with unwanted species passing through the chromatography media in the flowthrough. The IgG or other desired protein is subsequently eluted from the chromatography media (optionally, after washing or flushing the chromatography media) in an eluted fraction. Application of a product of the methods described above to a protein A or protein G affinity column, followed by elution of an IgG fraction using an acidic buffer is an example of positive selection of IgG. In some embodiments one or more additional protein(s) of interest can be recovered from the flowthrough fraction.

In negative selection unwanted species bind to the chromatography media, with IgG or another protein of interest passing through the chromatography media in the flowthrough fraction. The chromatography media can then be regenerated for re-use by elution of the unwanted species. Application of a product of the methods described above to an anion exchange column under appropriate buffer conditions with collection of an IgG-containing flowthrough fraction is an example of negative selection of IgG. In some embodiments one or more additional protein(s) of interest can be recovered from the bound materials released by elution.

Suitable chromatography media for use in methods of the inventive concept include size exclusion media, ion exchange media (e.g., anion exchange media, strong anion exchange media, cation exchange media, or strong cation exchange media), hydrophobic interaction media, dye affinity media, mixed mode media, and affinity media. Chromatography media can be provided as porous particles or beads, non-porous particles or beads, porous membranes, and/or filters. Chromatography media provided as particles or beads can be applied in the form of a chromatography column or in a flow chromatography system. In some embodiments two or more chromatography steps can be employed.

In some embodiments a buffer exchange step can be employed prior to application to a chromatography step. Suitable buffer exchange steps include size exclusion chromatography, dialysis, ultrafiltration, and precipitation followed by resuspension and dissolving of the precipitate.

A variety of affinity chromatography media suitable for use in methods of the inventive concept are available for isolation of IgG from solution. These include chromatography media with coupled bacterial receptors for the IgG Fc region (protein A, protein G), IgG light chains (protein L), and antibody class-specific antibodies (e.g., caprine anti-human IgG). In turn, these ligands can be coupled to a wide variety of solid phases, including agarose, cross-linked agarose, synthetic polymers, mixtures of natural and synthetic polymers, porous glass, membranes, and filters. Selection of the IgG-binding ligand and the media to which it is coupled can impact the concentration and precipitating agent and/or lipid/lipoprotein adsorbing solid used. For example, use of a robust ligand (such as protein A) coupled to a low nonspecific binding media (such as synthetic or partially synthetic media) can yield an affinity chromatography media that is somewhat resistant to fouling and tolerant of harsh cleaning processes. Use of such media can, for example, allow the use of less precipitating agent and/or lipid/lipoprotein adsorbing solid than if a relatively labile ligand (such as an immunoglobulin-specific antibody) coupled to an easily-fouled media is used in an affinity separation step.

In embodiments directed to isolation of IgG, a chromatography media other than immunoglobulin-specific affinity chromatography can be used. Suitable alternative chromatography media include but are not limited to anion exchange media, cation exchange media, hydrophobic interaction media, dye affinity media, mixed mode media, and size exclusion media. Such media can be selected so that IgG binds to the media and is subsequently recovered in an eluted fraction. Alternatively, such media can be selected so that IgG does not interact appreciably with the media and is found in either a flowthrough fraction from the column. In some embodiments such media can be selected to interact with, but not retain, IgG such that IgG is recovered as a distinct peak in the column effluent.

In such embodiments the concentration of precipitant can be selected so that residual precipitant in a supernatant or in a resuspended and dissolved precipitate does not interfere with the interactions (or lack thereof) between IgG and the non-IgG specific chromatography media. In some embodiments a dilution step can be incorporated in order to accomplish this.

Figure 1A:
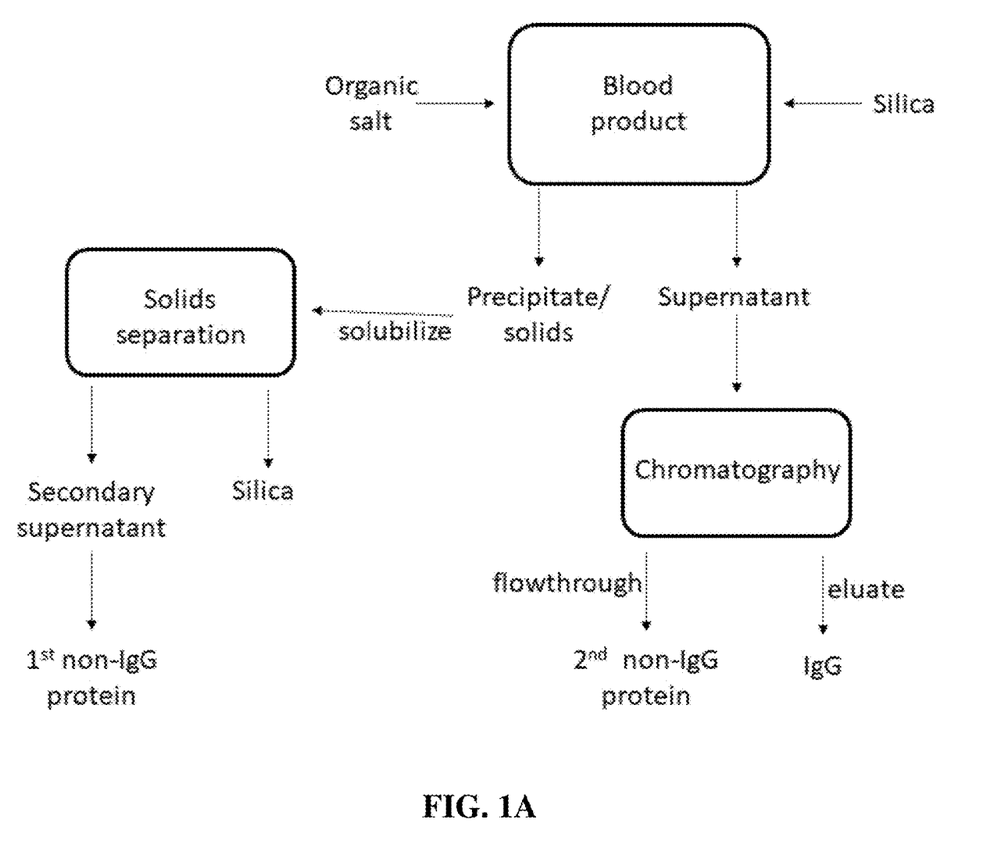
FIG. 1A depicts a method utilizing positive selection for the protein of interest.

An example of a method of the inventive concept is shown in FIG. 1A. As shown, a precipitating agent (here an organic salt) and a lipid/lipoprotein adsorbing solid (here silica) are added to a blood product. As noted above, this addition can be sequential or simultaneous. The resulting supernatant includes IgG and has a reduced content of fouling non-IgG proteins as well as lipids/lipoproteins, and moves on to a downstream chromatography step that positively selects for IgG (e.g., a chromatography step utilizing IgG-binding media, such as a protein A chromatography media or a protein G chromatography media), in which IgG is bound to the chromatography media and is subsequently eluted. Non-IgG proteins can be optionally recovered from the flowthrough of the chromatography column in such an embodiment. In a preferred embodiment the concentration of precipitating agent is selected so that it does not interfere with binding of IgG to the chromatography media, permitting direct application of supernatant following removal of solids. Alternatively, a concentration of precipitating agent can be selected that permits binding of IgG to the chromatography media following simple dilution of the supernatant fraction. Since the chromatography media serves to concentrate IgG within the column volume this does not adversely impact the concentration of the purified IgG product. The precipitate resulting from such a method includes the silica as well as non-IgG proteins. Such non-IgG proteins can be recovered by suspending and dissolving the precipitate, removing the solid silica fraction, and further processing the dissolved precipitate.

Figure 1B:
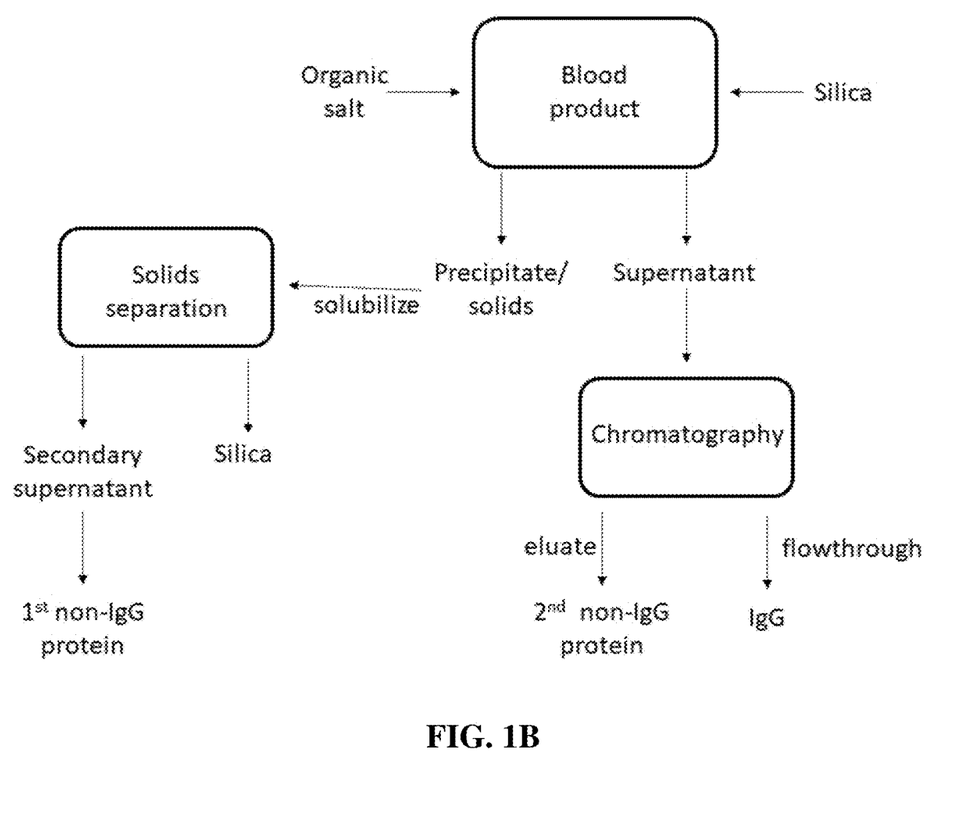
FIG. 1B depicts a method utilizing negative selection for the protein of interest.
Figure 2A:
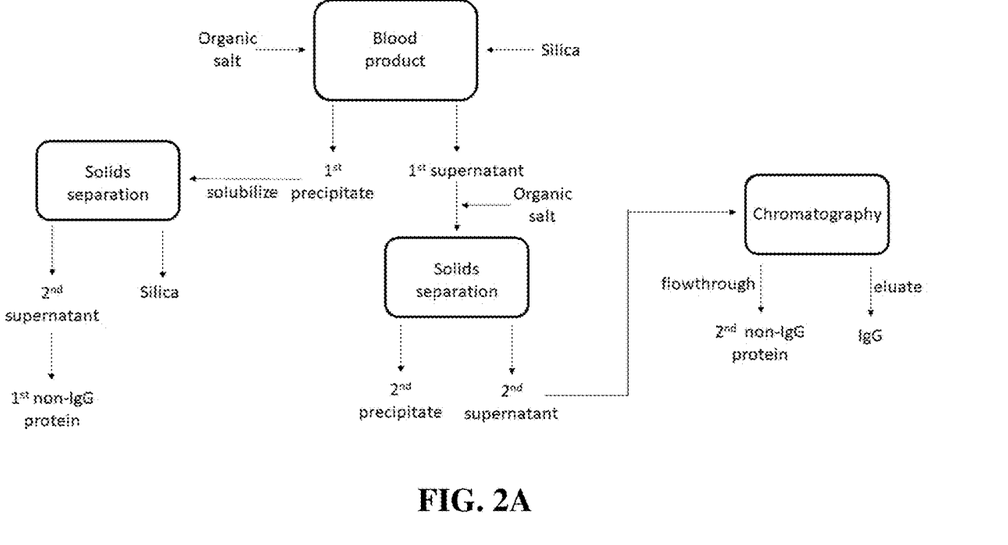
FIG. 2A depicts a method utilizing positive selection for the protein of interest.

An alternative embodiment is shown in FIG. 1B. As shown, a precipitating agent (here an organic salt) and a lipid/lipoprotein adsorbing solid (here silica) are added to a blood product. As noted above, this addition can be sequential or simultaneous. The resulting supernatant includes IgG and has a reduced content of fouling non-IgG proteins as well as lipids/lipoproteins, and moves on to a downstream chromatography step that negatively selects for IgG (e.g., a chromatography step utilizing a chromatography media that does not bind IgG, but that binds contaminating non-IgG components), in which IgG is found in the flowthrough (i.e., unbound fraction). Non-IgG proteins can be optionally recovered from chromatography media in such an embodiment by eluting the column (for example, using a low pH and/or high salt content buffer) and collecting the eluted fraction. This can also serve to regenerate the chromatography media. In a preferred embodiment the concentration of precipitating agent is selected so that it does not interfere with binding of non-IgG components of the applied supernatant to the chromatography media, permitting direct application of supernatant following removal of solids. Alternatively, a concentration of precipitating agent can be selected that permits binding of non-IgG components of the supernatant to the chromatography media following simple dilution of the supernatant fraction. The precipitate resulting from such a method includes the silica as well as non-IgG proteins. Such non-IgG proteins can be recovered by suspending and dissolving the precipitate, removing the solid silica fraction, and further processing the dissolved precipitate Another method of the inventive concept is shown in FIG. 2A. As shown, a precipitating agent (here an organic salt) and a lipid/lipoprotein adsorbing solid (here silica) are added to a blood product. As noted above, this addition can be sequential or simultaneous, and produces a supernatant and a precipitate (which includes the adsorbing solid and non-IgG proteins). The resulting supernatant includes IgG and has a reduced content of fouling non-IgG proteins as well as lipids/lipoproteins. This initial supernatant moves on to a second precipitation step performed by application of an additional precipitant. This additional or second precipitant can be the same as or different from the precipitant utilized in the initial precipitation step. As shown, this can yield a second supernatant and a second precipitate (which includes other non-IgG proteins). This second supernatant then moves to a positive selection chromatography step in which IgG is bound to the chromatography media (e.g., protein A or protein G media) and is subsequently eluted. Non-IgG proteins can be recovered from the flowthrough of a column of the chromatography media. Similarly, non-IgG proteins can be recovered from precipitates generated in upstream precipitation steps. In a preferred embodiment the concentration of precipitating agent is selected so that it does not interfere with binding of IgG to the chromatography media, permitting direct application of the second supernatant following removal of solids. Alternatively, a concentration of precipitating agent can be selected that permits binding of IgG to the chromatography media following simple dilution of the second supernatant. Since the chromatography media serves to concentrate IgG within the chromatography media's volume this does not adversely impact the concentration of the purified IgG product.

As noted above, the first precipitate resulting from the first precipitation step of such a method includes the silica as well as non-IgG proteins. Such non-IgG proteins can be recovered by suspending and dissolving the precipitate, removing the solid silica fraction, and further processing the dissolved precipitate. Similarly, the second precipitate obtained from the second precipitation step can be resuspended and dissolved, with additional non-IgG proteins isolated from the dissolved second precipitate.

Alternatively, the amount of additional precipitant used in the second precipitation step shown in FIG. 2A can be selected to precipitate IgG from the first supernatant. In such an embodiment the second precipitate is collected, resuspended, and dissolved. This dissolved second precipitate can, following removal of the solid silica, move to a downstream IgG-specific affinity chromatography column. In such an embodiment additional non-IgG proteins can be recovered from the second supernatant and/or from the flowthrough fraction obtained from the affinity column.

Figure 2B:
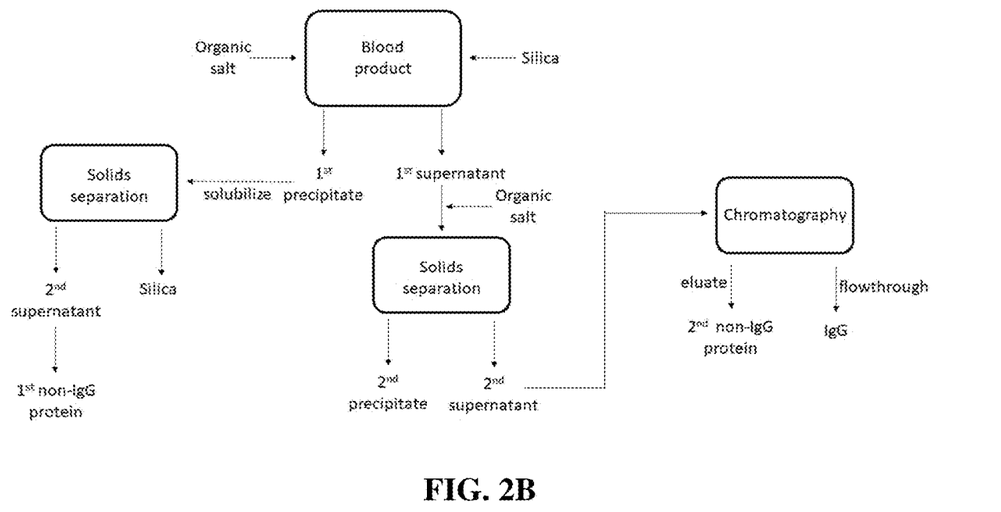
FIG. 2B depicts a method utilizing negative selection for the protein of interest.

An alternative embodiment of a method of the inventive concept is shown in FIG. 2B. As shown, a precipitating agent (here an organic salt) and a lipid/lipoprotein adsorbing solid (here silica) are added to a blood product. As noted above, this addition can be sequential or simultaneous, and produces a supernatant and a precipitate (which includes the adsorbing solid and non-IgG proteins). The resulting supernatant includes IgG and has a reduced content of fouling non-IgG proteins as well as lipids/lipoproteins. This initial supernatant moves on to a second precipitation step performed by application of an additional precipitant. This additional or second precipitant can be the same as or different from the precipitant utilized in the initial precipitation step. As shown, this can yield a second supernatant and a second precipitate (which includes other non-IgG proteins). This second supernatant then moves to a negative selection chromatography step in which non-IgG components bind to the chromatography media and IgG emerges in the unbound, flowthrough fraction. Non-IgG proteins can be recovered by eluting them from the chromatography media as an eluted fraction, which can also serve to regenerate the chromatography media. Similarly, non-IgG proteins can be recovered from precipitates generated in upstream precipitation steps. In a preferred embodiment the concentration of precipitating agent is selected so that it does not interfere with binding of non-IgG contaminants to the chromatography media, permitting direct application of the second supernatant following removal of solids. Alternatively, a concentration of precipitating agent can be selected that permits binding of non-IgG contaminants to the chromatography media following simple dilution of the second supernatant.

As noted above, the first precipitate resulting from the first precipitation step of such a method includes the silica as well as non-IgG proteins. Such non-IgG proteins can be recovered by suspending and dissolving the precipitate, removing the solid silica fraction, and further processing the dissolved precipitate. Similarly, the second precipitate obtained from the second precipitation step can be resuspended and dissolved, with additional non-IgG proteins isolated from the dissolved second precipitate.

Alternatively, the amount of additional precipitant used in the second precipitation step shown in FIG. 2B can be selected to precipitate IgG from the first supernatant. In such an embodiment the second precipitate is collected, resuspended, and dissolved. This dissolved second precipitate can, following removal of the solid silica, move to a downstream chromatography step utilizing chromatography media that binds non-IgG contaminants and permits IgG to pass through in a flowthrough fraction. In such an embodiment additional non-IgG proteins can be recovered from the second supernatant and/or by elution from the chromatography media.

Figure 3A:
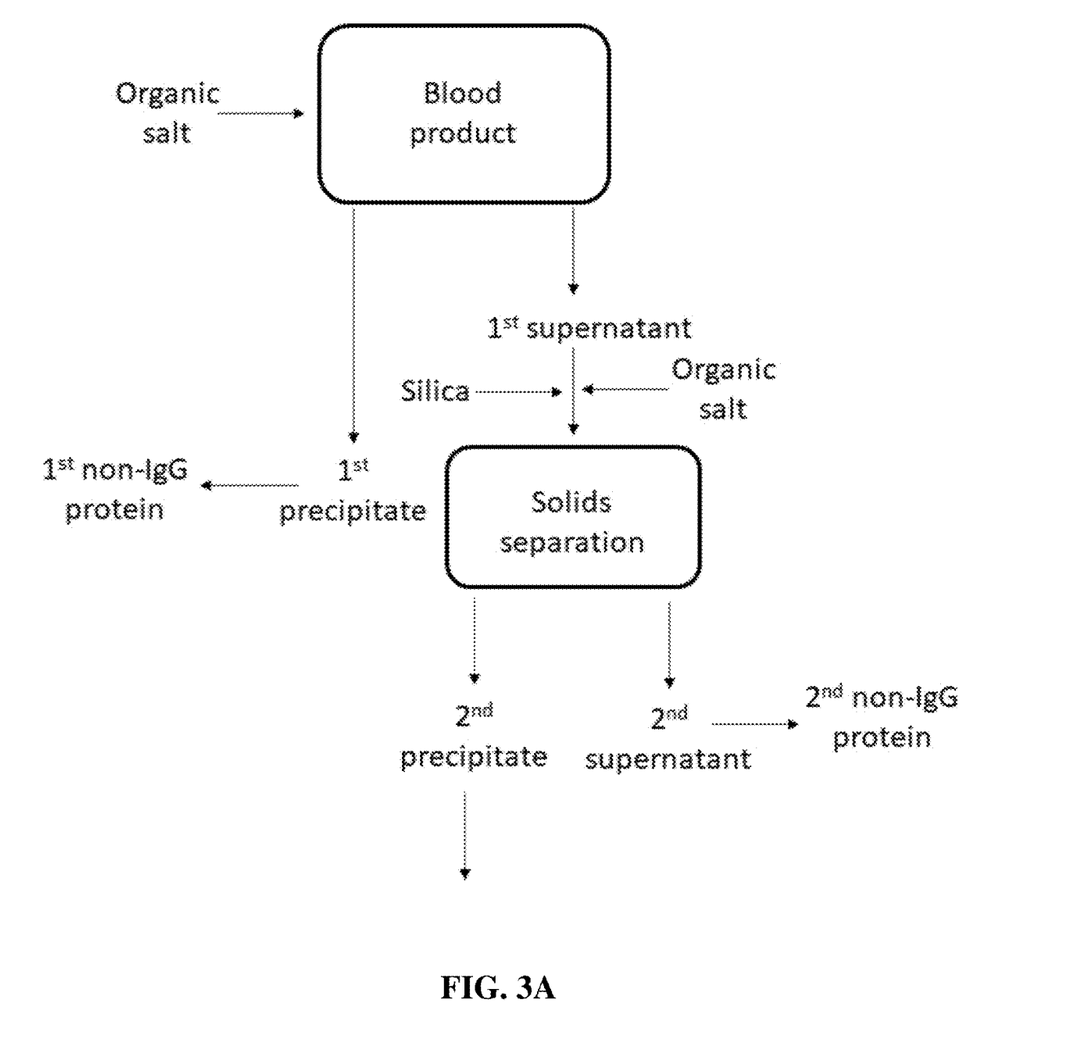
FIG. 3A depicts initial precipitation steps of the method.
Figure 3B:
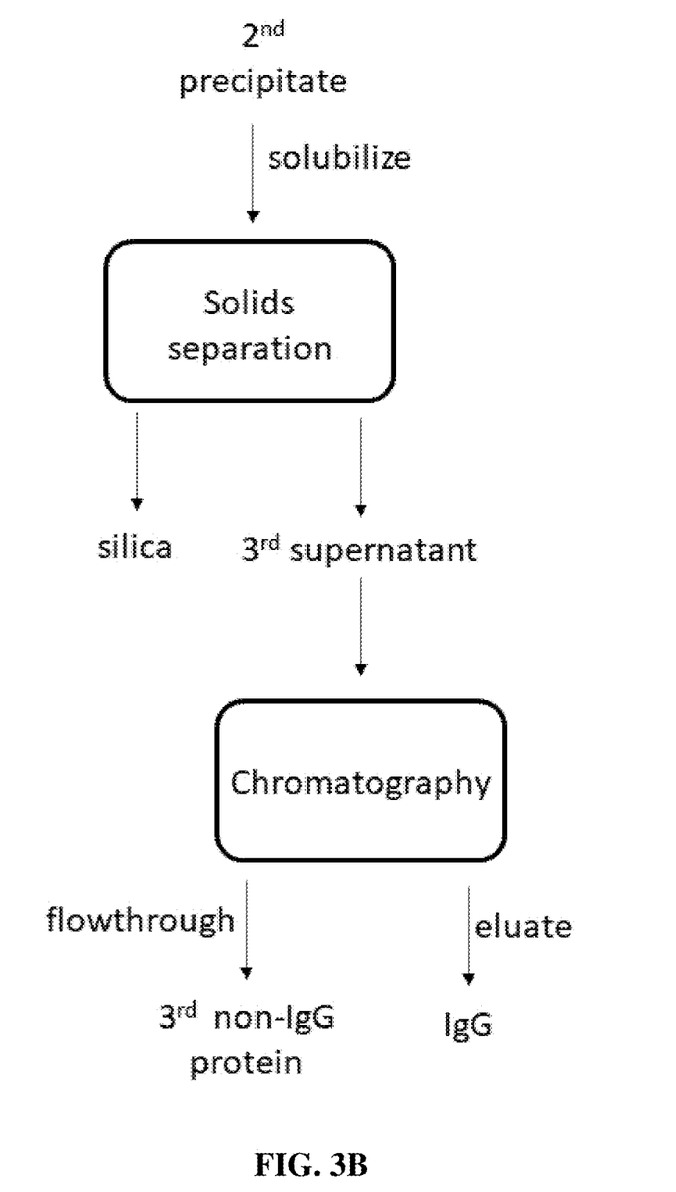
FIG. 3B continues from FIG. 3A and depicts a method utilizing positive selection for the protein of interest.
Figure 3C:
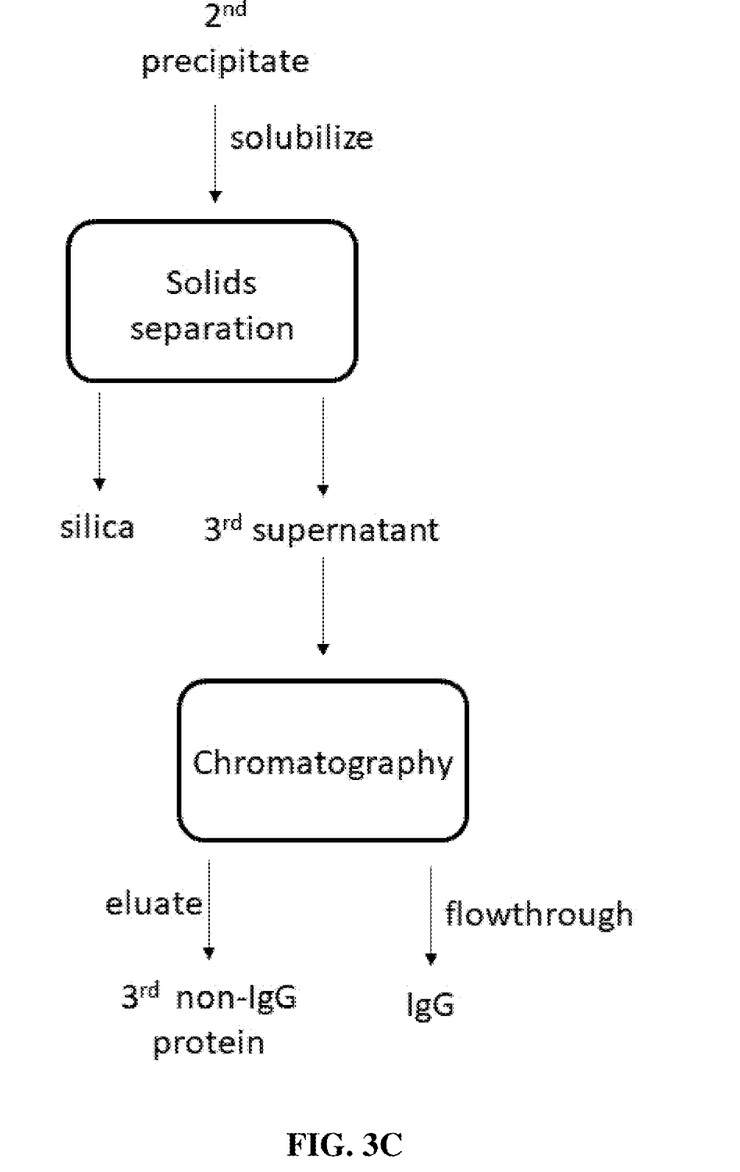
FIG. 3C continues from FIG. 3A and depicts a method utilizing negative selection for the protein of interest.

Another method of the inventive concept is shown in FIG. 3A and FIGS. 3B and 3C (each of which continue from FIG. 3A independently). As shown in FIG. 3A, in such a method an initial precipitation step is performed by applying a precipitant (in this instance an organic salt) to a blood product to generate a first precipitate and a first supernatant. As shown the initial concentration of precipitant is selected to retain IgG in the first supernatant. The resulting first precipitate can be further processed to recover non-IgG proteins. Additional precipitant and a lipid/lipoprotein adsorbing solid (in this instance silica) are applied to the first supernatant to generate a second supernatant and a second precipitate. This additional precipitant can be the same as or different from the first precipitant utilized in the initial precipitation step. The amount of additional precipitant can be selected to precipitate IgG from the second supernatant. In such an embodiment the second precipitate includes IgG and also the lipid/lipoprotein adsorbing solid. Additional non-IgG proteins can be recovered from the second supernatant.

FIG. 3B continues from FIG. 3A. As shown in FIG. 3B this second precipitate can be resuspended and dissolved to generate a third supernatant that contains IgG and a third precipitate that includes the lipid/lipoprotein adsorbing solid (which is not soluble). The third supernatant can move to a downstream positive selection chromatography step using a chromatography media that binds IgG, generating a flowthrough fraction that includes non-IgG components. Such non-IgG components can be recovered from this flowthrough fraction. IgG is recovered from an eluted fraction generated by adding an elution buffer (e.g., a low pH buffer) to the chromatography media.

Alternatively, precipitant concentration can be selected such that IgG is retained in the second supernatant. In such embodiments the second supernatant can be transferred to a downstream positive selection chromatography step utilizing an IgG-binding chromatography media, such that non-IgG components pass through the chromatography media as a flowthrough fraction. Such non-IgG components can subsequently be recovered from this flowthrough fraction. IgG can be recovered in an eluted fraction generated by applying an elution buffer (such as a low pH buffer) to the chromatography media. As noted above, in such embodiments the concentration of precipitant in the second supernatant can be selected so that it supports an effective positive selection chromatography step, or such that simple dilution of the second supernatant can adjust precipitant concentration to provide for effective positive selection chromatography, In such embodiments additional non-IgG proteins can be recovered from the second precipitate (following resuspension, dissolution, and removal of the lipid/lipoprotein adsorbing solid).

FIG. 3C shows an alternative path that continues from FIG. 3A. As shown in FIG. 3C this second precipitate can be resuspended and dissolved to generate a third supernatant that contains IgG and a third precipitate that includes the lipid/lipoprotein adsorbing solid (which is not soluble). The third supernatant can move to a downstream negative selection chromatography step using a chromatography media that binds non-IgG components, generating a flowthrough fraction that includes the IgG. Such non-IgG components can be recovered from the chromatography media by elution, which can also serve to regenerate the chromatography media.

Alternatively, precipitant concentration can be selected such that IgG is retained in the second supernatant. In such embodiments the second supernatant can be transferred to a downstream negative selection chromatography step utilizing a chromatography media that binds non-IgG components, such that IgG passes through the chromatography media as a flowthrough fraction. Non-IgG components can subsequently by eluting the chromatography media, which can also serve to regenerate the chromatography media. As noted above, in such embodiments the concentration of precipitant in the second supernatant can be selected so that it supports an effective negative selection chromatography step, or such that simple dilution of the second supernatant can adjust precipitant concentration to provide for effective negative selection chromatography, In such embodiments additional non-IgG proteins can be recovered from the second precipitate (following resuspension, dissolution, and removal of the lipid/lipoprotein adsorbing solid).

It should be appreciated that while isolation of immunoglobulin G is cited above, methods of the inventive concept can be applied to other proteins found in blood products. Such proteins of interest include, but are not limited to, albumin, alpha-1 antiproteinase inhibitor, fibrinogen, clotting factors, and other blood proteins of therapeutic interest.

In some embodiments, methods of the inventive concept can be applied to other protein-rich solutions (i.e., solutions having greater that 0.1%, 0.3%, 1%, 3%, 10%, or more) protein content by weight). Such protein rich solutions include cell culture media (e.g., bacterial culture media, hybridoma media, etc.), viral and/or cell lysates (e.g., bacterial lysates, eukaryotic cell lysates), egg products (e.g., egg white material containing IgY), process intermediates from serum or plasma purification processes (e.g., Cohn fractions, chromatography column effluents, etc.), products of cell-free synthesis, and products of chemical synthesis.

As noted above, embodiments of the inventive concept can include a solid separation step. Suitable solid separation methods include settling, decantation, filtration, and centrifugation. In embodiments where the solid includes both precipitated protein and lipid/lipoprotein adsorbing solid centrifugation can advantageously permit further segregation of solids contents if there is a significant density and/or hydrodynamic difference(s) between the precipitated protein and the lipid/lipoprotein adsorbing solid. For example, fumed silica is a low-density material that is useful in adsorbing lipids and can be separated from a relatively dense protein precipitate on the basis of density and/or hydrodynamic behavior. Such a centrifugation process can generate a supernatant stream, a precipitated protein stream, and a lipid/lipoprotein adsorbing solid stream. It should be appreciated that use of such a centrifugal separation process can permit the separation methods depicted above to be performed in a continuous or at least partially continuous manner.

Figure 4:
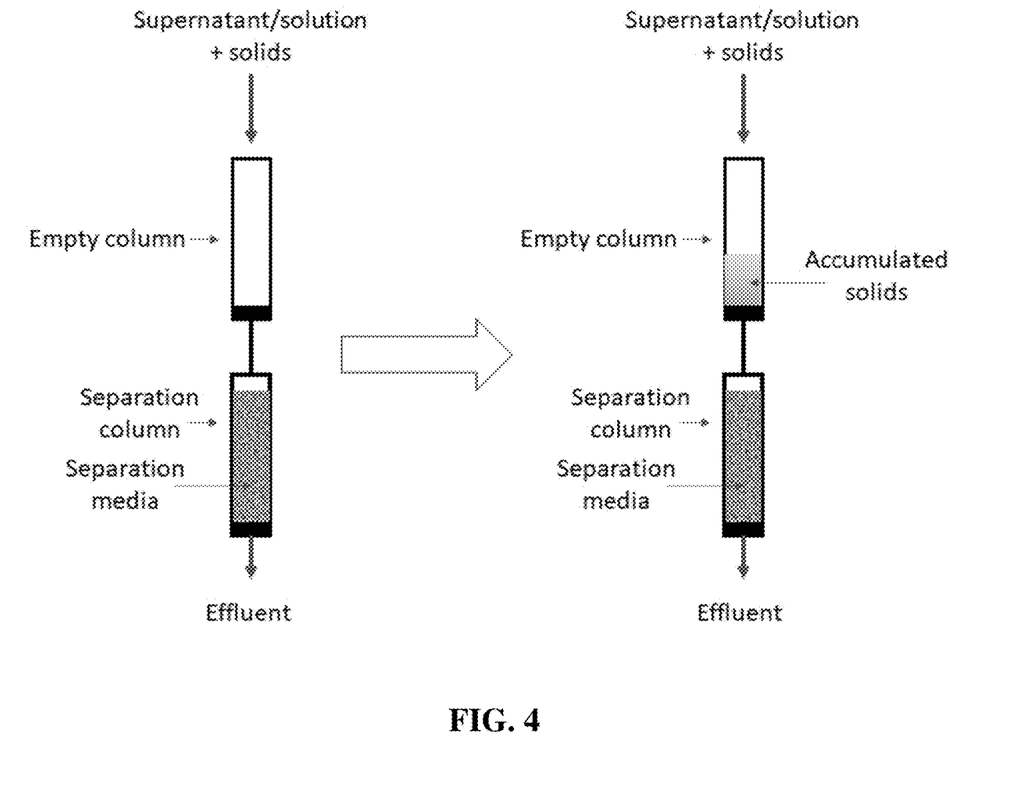
FIG. 4 schematically depicts a process of the inventive concept utilizing an empty chromatography column to capture solids from an intermediate product.

As noted above, solids can also be removed from process intermediates by filtration. Suitable filters include membrane filters, fibrous or particulate depth filters, and porous filters. It should be appreciated that the porous materials utilized as frits in chromatography columns can be utilized as filters in methods of the inventive concept. For example, an empty or buffer-filled chromatography column can be placed immediately upstream of an affinity or non-affinity separation column utilized in the process, such that the media-retaining frit of the empty or buffer-filled column can capture solids prior to entry into the affinity or non-affinity media. Such an arrangement is shown in FIG. 4. Similarly, the column used to retain affinity or non-affinity media can be selected to be oversized and additionally provided with an upper frit placed immediately above the input portion of the affinity or non-affinity media to leave an open head space within the column. Solids can accumulate in this head space by retention on the upper frit, and removed by inversion of the column and/or by reversing the direction of buffer flow.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refer to at least one of something selected from the group consisting of A, B, C . . . and N, the text should be interpreted as requiring only one element from the group, not A plus N, or B plus N, etc.

What is claimed is:

1. A method of isolating a first protein from a blood product, comprising:
mixing the blood product comprising the first protein and a second protein with a lipid or lipoprotein adsorbing particulate and an organic salt to generate a suspension comprising a first precipitate and a first supernatant, wherein the first precipitate comprises a precipitated second protein and the lipid or lipoprotein adsorbing material complexed with a lipid or a lipoprotein present in the blood product;
separating the suspension by centrifugation to generate a first stream comprising the first supernatant, a second stream comprising the precipitated second protein, and third stream comprising the lipid or lipoprotein adsorbing material complexed with a lipid or a lipoprotein present in the blood product;
applying the first supernatant to a chromatography media to obtain an effluent comprising the first protein from the chromatography media; and
recovering the second protein from the second stream, wherein the concentration of the organic salt is sufficient to precipitate a first non-protein of interest protein from the blood product.

2. The method of claim 1, wherein the organic salt is a citrate or acetate salt.

3. The method of claim 1, wherein the method is performed in a continuous manner.

4. The method of claim 1, wherein the organic salt is citrate or acetate, and wherein the concentration of the organic salt is from 5% to 15% by weight.

5. The method of claim 1, wherein the lipid or lipoprotein adsorbing particulate is added to the blood product essentially contemporaneously with the organic salt or prior to addition of the organic salt.

6. The method of one of claim 1, wherein the chromatography media does not bind the protein of interest, comprising collecting a flowthrough fraction comprising the protein of interest from the chromatography.

7. A method of isolating a first protein from a blood product, comprising:
mixing the blood product comprising the first protein and a second protein with a lipid or lipoprotein adsorbing particulate and an organic salt at a first concentration to produce a suspension comprising a first precipitate comprising a precipitated second protein and the lipid or lipoprotein adsorbing particulate complexed with a lipid or lipoprotein of the blood product and a first supernatant;
separating the suspension by centrifugation to generate a first stream comprising the first supernatant, a second stream comprising the precipitated second protein, and third stream comprising the lipid or lipoprotein adsorbing material complexed with a lipid or a lipoprotein present in the blood product;
adding an additional amount of the organic salt to the first supernatant to provide a second concentration of the organic salt, thereby generating a second precipitate comprising the first protein and a second supernatant;
resuspending and dissolving the second precipitate to generate a redissolved second precipitate;
applying the redissolved second precipitate to a chromatography media; and
collecting an effluent comprising the first protein from the chromatography media; and
recovering the second protein from the second stream, wherein the first concentration of the organic salt is sufficient to precipitate the second protein from the blood product.

8. The method of claim 7, wherein the organic salt is a citrate or acetate salt.

9. The method of claim 7, wherein the method is performed in a continuous manner.

10. The method of claim 7, wherein the organic salt is a citrate or an acetate salt, wherein the first concentration of the organic salt is from 5% to 15% by weight.

11. The method of claim 7, wherein the lipid or lipoprotein adsorbing particulate is added to the blood product essentially contemporaneously with the organic salt.

12. The method of claim 7, wherein the chromatography media does not bind the protein of interest, and wherein the effluent is a flowthrough fraction from the chromatography media comprising the protein of interest.

13. A method of isolating a first protein from a blood product, comprising:
mixing the blood product comprising the first protein and a second protein with an organic salt at a first concentration to produce a first precipitate and a first supernatant;
mixing the first supernatant with a lipid or lipoprotein adsorbing particulate and an additional amount of the organic salt to the first supernatant to provide a second concentration of the organic salt to generate a suspension comprising a second precipitate and a second supernatant, wherein the second precipitate comprises a precipitated first protein of interest and the lipid or lipoprotein adsorbing particulate complexed with a lipid or lipoprotein of the first supernatant and the second supernatant comprises the second protein;
separating the suspension by centrifugation to generate a first stream comprising the first supernatant, a second stream comprising the precipitated first protein, and third stream comprising the lipid or lipoprotein adsorbing material complexed with a lipid or a lipoprotein present in the blood product;
recovering the second protein from the first supernatant;
resuspending and dissolving the precipitated first protein to generate a redissolved first protein;
applying the redissolved first protein to a separation column; and
collecting an effluent comprising the first protein from the separation column,
wherein the first concentration of the citrate or acetate salt is sufficient to precipitate the second protein from the blood product.

14. The method of claim 13, wherein the organic salt is a citrate or acetate salt.

15. The method of claim 13, wherein the method is performed in a continuous fashion.

16. The method of claim 15, comprising resuspending the first precipitate to generate a secondary solution comprising the non-protein of interest protein, and recovering the non-protein of interest protein from the secondary solution.

17. The method of claim 13, wherein the organic salt is a citrate or acetate salt, and wherein the first concentration is from 5% to 15% by weight.

18. The method of claim 13, wherein the chromatography media does not bind the first protein, and wherein the effluent is a flowthrough fraction from the chromatography media comprising the first protein.

19. The method of claim 7, wherein the organic salt is a citrate or an acetate salt, wherein the second concentration of the organic salt is from 15% to 50% by weight.

20. The method of claim 13, wherein the organic salt is a citrate or an acetate salt, wherein the second concentration of the organic salt is from 15% to 50% by weight.

* * * * *

UNITED STATES PATENT AND TRADEMARK OFFICE
CERTIFICATE OF CORRECTION

| | |
|---|---|
| PATENT NO. | : 11,732,004 B2 |
| APPLICATION NO. | : 17/225934 |
| DATED | : August 22, 2023 |
| INVENTOR(S) | : Eugene Zurlo et al. |

It is certified that error appears in the above-identified patent and that said Letters Patent is hereby corrected as shown below:

In the Claims

At Column 16, Line 15, change, "The method of claim, 15," to --The method of claim, 13,--

Signed and Sealed this
Twelfth Day of December, 2023

Katherine Kelly Vidal
*Director of the United States Patent and Trademark Office*